US008633166B2

(12) United States Patent
Hamann et al.

(10) Patent No.: US 8,633,166 B2
(45) Date of Patent: Jan. 21, 2014

(54) **METHICILLIN-RESISTANT *STAPHYLOCOCCUS AUREUS* ACTIVE METABOLITES**

(76) Inventors: Mark T. Hamann, University, MS (US); Mohamed Ali, Oxford, MS (US)

( * ) Notice: Subject to any disclaimer, the term of this patent is extended or adjusted under 35 U.S.C. 154(b) by 748 days.

(21) Appl. No.: 12/725,156

(22) Filed: Mar. 16, 2010

(65) Prior Publication Data

US 2010/0234311 A1 Sep. 16, 2010

Related U.S. Application Data

(60) Provisional application No. 61/160,413, filed on Mar. 16, 2009.

(51) Int. Cl.
*A61K 31/70* (2006.01)
*C07H 17/06* (2006.01)
*A01N 43/04* (2006.01)

(52) U.S. Cl.
USPC .............................................. 514/27; 536/13

(58) Field of Classification Search
USPC .............................................. 536/13; 514/2.7
See application file for complete search history.

(56) References Cited

U.S. PATENT DOCUMENTS

2003/0105031 A1* 6/2003 Rosenbloom .................. 514/27

OTHER PUBLICATIONS

Ibrahim et al., "Methicillin-Resistant *Staphylococcus aureus* (MRSA)-Active Metabolites from Platanus occidentalis (American Sycamore)", J. Nat. Prod. 2009, 72, 2141-2144, 2009 American Chemical Society and American Society of Pharmacognosy Published on Web Nov. 11, 2009.

Mitrocosta et al., "Cytotoxicity Against Human Leukemic Cell Lines, and the Activity on the Expression of Resistance Genes of Flavonoids from Platanus orientalis", Anticancer Research 19: 2085-2088 (1999).

Kawahara et al., "A New Acylated Flavonol Glycoside from the Leaves of Eriobotrya japonica", Chemical and Pharmaceutical Bulletin 50 (12) 1619-1620, Dec. 2002, Pharmaceutical Society of Japan 2002.

Otsuka et al., "Anti-methicillin Resistant *Staphylococcus aureus* (MRSA) Compounds Isolated from Laurus nobilis", Biological and Pharmaceutical Bulletin 31 (09) 1794-1797, (2008), vol. 31, No. 9 Pharmaceutical Society of Japan 2008.

Liu et al., "Synergistic Effect of Kaempferol Glycosides Purified from Laurus nobilis and Fluoroquinolones on Methicillin-Resistant *Staphylococcus aureus*", Biological and Pharmaceutical Bulletin 32(3) 489-492 (Mar. 2009). Pharmaceutical Society of Japan 2009.

Rao et al., "Acylated and Non-Acylated Flavonol Monoglycosides from the Indian Minor Spice Nagkesar (mammea longifolia)", Journal of Agricultural and Food Chemistry, 2002, 50, 3143-146.

De Marino et al, "Megastigmane and Phenolic Components from *Laurus nobilis L.* Leaves and Their Inhibitory Effects on Nitric Oxide Production", Journal of Agricultural and Food Chemistry, 2004, 52, 7525-7531. 2004 American Chemical Society, Published on Web Nov. 13, 2004.

Tanaka et al, "Constituents of *Laurus nobilis L.* inhibit recombinant human lanosterol synthase", J. Nat Med (2006) 60: 78-81, Published online: Oct. 12, 2005: The Japanese Society of Pharmacognosy and Springer-Verlag 2005.

Kaouadji et al., "Further Acylated Kaempferol Rhamnosides from Platanus Acerifolia Buds", Journal of Natural Products, vol. 56, No. 9, pp. 1618-1621, Sep. 1993.

Soliman et al., "An Acylated Kaempferol Glycoside from Flowers of *Foeniculum vulgare* and F. Dulce", Molecules 2002, 7, 245-251. ISSN 1420-3049 http://www.mdpi.org.

Dimas et al., "Cytotoxic Activity of Kaempferol Glycosides Against Human Leukaemic Cell Lines In Vitro", Pharmacological Research, vol. 41, No. 1, 2000. Academic Press 2000.

Han et al., "Down-regulation of prostate specific antigen in LNCaP cells by flavonoids from the pollen of Brassica napus L.", ScienceDirect, Phytomedicine 14 (2007) 338-343. ELSEVIER.

Garcez et al., "Benzylisoquinoline Alkaloids and Flavonols from Ocotea Vellosiana", Pergamon, Phytochemistry, vol. 39, No. 4, pp. 815-816, 1995, Elsevier Science Ltd.

Bloor, S.J, "An Antimicrobial Kaempferol-Diacyl-Rhamnoside from Pentachondra Pumila", Pergamon, Phytochemistry, vol. 38, No. 4, pp. 1033-1035, 1995, Elsevier Science Ltd 1995.

Taniguchi et al., "Three Isocoumarins from *Coriandrum Sativum*", Pergamon, Phytochemistry, vol. 42, No. 3, pp. 843-846, 1996, Elsevier Science Ltd 1996.

Wang et al., "Prenylflavonol, acylated flavonol glycosides and related compounds from Epimedium sagittatum", ScienceDirect, Phytochemistry 68 (2007) 2455-2464. Elsevier.

Lee et al., "Acylated flavonol monorhamnosides, alpha-glucosidase inhibitors, from Machilus philippinesis", Phytochemistry 69 (2008) 2347-2353. Elsevier.

Fiorini et al., "Acylated Kaempferol Glycosides from Laurus Nobilis Leaves", Pergamon, Phytochemistry, vol. 47, No. 5. pp. 821-824, 1998. Elsevier Science Ltd. 1998.

Mai et al., "A New Lignan Dimer from Mallotus philippensis", Natural Product communications, 2010, vol. 5, No. 3, pp. 423-426.

El-Alfy et al., "Phenolic Constituents of *Platanus orientalis L.* Leaves", Natural Product Communications, 2008, vol. 3, No. 2, pp. 199-203.

Xiao et al.,"Effects of Chemical Constituents of Cyrtomium", Chinese Journal of Preventive Veterinary Medicine, vol. 29, No. 12, Dec. 2007. ENGLISH ABSTRACT.

* cited by examiner

*Primary Examiner* — Patrick Lewis
*Assistant Examiner* — Everett White
(74) *Attorney, Agent, or Firm* — Harris, Shelton, Hanover & Walsh; Susan Fentress

(57) ABSTRACT

This present provides kaempferol-3-(2-E,3-Z-di-p-coumaroyl)-rhamnoside, kaempferol-3-(2-Z-3-E-di-p-coumaroyl)-rhamnoside, and kaempferol-3-(2,3-di-Z-p-coumaroyl)-rhamnoside compounds useful as a new class of anti-bacterial agents. These compounds are extracted from *Platanus occidentalis*. These compounds were found to exhibit anti-bacterial activity against methicillin resistant *Staphylococcus aureus* (MRSA).

6 Claims, 4 Drawing Sheets

FIG 1.

| compound | MRSA | | | *S. aureus* | | |
|---|---|---|---|---|---|---|
| | $IC_{50}$ | MIC | MBC | $IC_{50}$ | MIC | MBC |
| (1) | 1.99 | 10 | - | 3.72 | 13.3 | - |
| (2) | 0.79 | 1.67 | - | 1.63 | 5.83 | - |
| (3)* | 0.73 | 1.25 | - | 1.41 | 3.75 | - |
| (4) | 0.40 | 0.63 | - | 1.56 | 2.5 | - |
| Methicillin | >20 | - | - | 0.45 | 2.5 | - |
| Piperacillin | - | - | - | NT | NT | NT |
| Cloxacillin* | 8.89 | - | - | NT | NT | NT |
| Ciprofloxacin* | 0.06 | 0.25 | 1.0 | 0.1 | 0.38 | 0.75 |

All values in μg/mL
$IC_{50}$ = the concentration that affords 50% inhibition of growth; represents an average of triplicate (or duplicate *) values
MIC (Minimum Inhibitory Concentration) is the lowest test concentration that allows no detectable growth;
MBC (Minimum Bactericidal Concentration) is the lowest test concentration that kills the organism.
NT = not tested

FIG. 3

| | $IC_{50}$ (µg/ml) | | | | | |
|---|---|---|---|---|---|---|
| Sample name | SK-MEL | KB | BT-549 | SK-OV-3 | VERO | LLC-PK11 |
| MI-C-1 | 59 | 57 | NC | 65 | NC | 60 |
| MI-MIX | 64 | >100 | NC | NC | NC | >100 |
| DOXORUBICIN | 0.6 | 0.9 | 1.4 | 1.2 | >5 | 0.6 |

$IC_{50}$ = the concentration that causes a reduction of 50% in cell viability

MI-C-1 = compound (1)
MI-MIX = a semipure material with compounds (1), (2), (3) and (4)

NC = no cytotoxicity up to 100 µg/ml

Cancer Cells:
SK-MEL = human malignant melanoma
KB = human epidermal carcinoma, oral
BT-549 = human ductal carcinoma, breast
SK-OV-3 = human ovary carcinoma Noncancer Cells:
Vero = monkey kidney fibroblasts
LLC-PK11 = pig kidney epithelial cells

FIG. 4

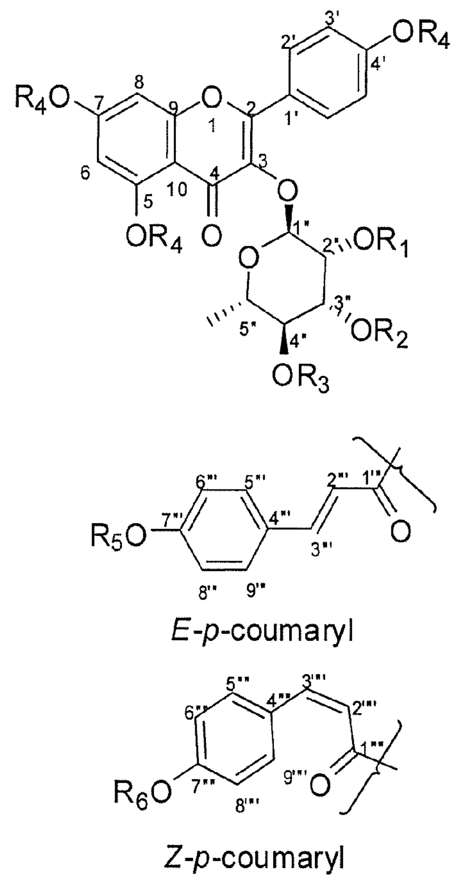

| $R_1$ | $R_2$ | $R_3$ | $R_4$ | $R_5$ | $R_6$ |
|---|---|---|---|---|---|
| *E-p*-coumary | *E-p*-coumary | *E-p*-coumary | H | H | H |
| *Z-p*-coumary | *Z-p*-coumary | *Z-p*-coumary | $CH_3$ | $CH_3$ | $CH_3$ |
| H | H | H | $C_2H_5$ | $C_2H_5$ | $C_2H_5$ |
| $CH_3$ | $CH_3$ | $CH_3$ | $C_3H_7$ | $C_3H_7$ | $C_3H_7$ |
| $C_2H_5$ | $C_2H_5$ | $C_2H_5$ | $C_4H_9$ | $C_4H_9$ | $C_4H_9$ |
| $C_3H_7$ | $C_3H_7$ | $C_3H_7$ | $C_5H_{11}$ | $C_5H_{11}$ | $C_5H_{11}$ |
| $C_4H_9$ | $C_4H_9$ | $C_4H_9$ | $C_6H_{13}$ | $C_6H_{13}$ | $C_6H_{13}$ |
| $C_5H_{11}$ | $C_5H_{11}$ | $C_5H_{11}$ | $C_6H_{10}$ | $C_6H_{10}$ | $C_6H_{10}$ |
| $C_2H_3O_2$ | $C_2H_3O_2$ | $C_2H_3O_2$ | $C_2H_3O_2$ | $C_2H_3O_2$ | $C_2H_3O_2$ |
| $C_3H_5O_2$ | $C_3H_5O_2$ | $C_3H_5O_2$ | $C_3H_5O_2$ | $C_3H_5O_2$ | $C_3H_5O_2$ |
| TfO | TfO | TfO | TfO | TfO | TfO |
| Bz | Bz | Bz | Bz | Bz | Bz |

METHICILLIN-RESISTANT *STAPHYLOCOCCUS AUREUS* ACTIVE METABOLITES

RELATED APPLICATIONS

This application claims priority to U.S. provisional application 61/160,413, filed on Mar. 16, 2009 and which is herein incorporated by reference in its entirety.

GOVERNMENTAL INTEREST

This invention was made with government support under Grant No. 5 RO1 AI36596, awarded by the National Institutes of Health. The United States government has certain rights in the invention.

FIELD OF THE INVENTION

The present invention relates to a new class of compounds extracted from *Platanus occidentalis*. These compounds were found to exhibit anti-bacterial activity against methicillin resistant *Staphylococcus aureus* (MRSA) and other gram positive bacteria.

BACKGROUND

Methicillin-resistant *Staphylococcus aureus* (MRSA) is a serious pathogen that causes patient mortality. Over 50% of infections around the world are caused by MRSA. MRSA has emerged as a community-associated pathogen (CA-MRSA), usually resulting in skin infections with abscess formation and cellulites in individuals who have not been hospitalized within the last year. Moreover, hospital-acquired infections of MRSA (HA-MRSA), relative to CA-MRSA, have been shown to be resistant to multiple antibiotics.

Two mechanisms of resistance of MRSA to the β-lactam antibiotics are inactivation by β-lactamase and the production of a penicillin binding protein PBP2a with decreased affinity for the antibiotics. The resistance PBP2a genotype of MRSA strains is encoded mecA gene which is transported on a mobile genetic element known as a staphylococcal cassette chromosome (SCC). The differences in susceptibility of HA-MRSA and CA-MRSA can be attributed to different SCCmec types (types IV and V for CA-MRSA and types I, II and III for HA-MRSA). These genes are associated with resistance to multiple drug classes, in addition to β-lactam antibiotics. CA-MRSA isolates are primarily resistant to β-lactam antibiotics (penicillins, cephalosporins, carbapenems) and macrolides and where initiation of antibiotic therapy may not be necessary in all patients with skin soft tissue infections caused by CA-MRSA.

Vancomycin has been the drug of choice despite a success rate of 35-57% and side effects including nosocomial pneumonia, skin and soft tissue infections, in addition to low bone penetration limit vancomycin's utility. Moreover, the increased use of vancomycin, especially in chronic patients has resulted in the emergence of MRSA with reduced susceptibility to glycopeptides.

The most effective anti-MRSA drug used today is daptomycin, a cyclic lipopeptide derived from the fermentation of *Streptomyces roseosporus*. Daptomycin is most useful for use in short duration and to treat persistent MRSA unaffected by other drug treatments such as vancomycin. Its mechanism of action involves binding to the bacterial cell membrane, causing depolarization of the membrane potential leading to inhibition of protein, DNA and RNA synthesis. Unfortunately, the FDA has reported some side effects for daptomycin, including an increase in blood creatine phosphokinase, rhabdomyolysis, skin exfoliation and skin ulcers.

Efforts have been made to decrease infection and colonization of MRSA in hospitals and other environments including the use of products that sterilize surfaces, including hand washes. Products containing 4% chlorhexidine gluconate (CHG) and 1% triclosan reduce the total bacterial count. The 4% CHG is more effective at reducing the total count than 1% triclosan; however, 1% triclosan has the ability to remove MRSA while 4% CHG cannot. Povidone-iodine used as an intranasal cream by the physicians and nurses working in the neonatal intensive care unit shows a 10% reduction in the isolation of MRSA pathogens.

*Platanus occidentalis*, the American Sycamore (fam. Platanaceae) has been known for its high safety profile in the treatment of a wide variety of conditions in traditional folk medicine. Species of Platanaceae have been used frequently for their antimicrobial and antiseptic properties. Native Americans used the American sycamore for cold and cough remedies, as well as dietary, dermatological, gynecological, respiratory, and gastrointestinal aids. The bark was used with honey locust to relieve hoarseness and sore throats as well as to treat skin eruptions, scabs and eczema, lung troubles, hemorrhages and tuberculosis. The mixture of the bark with the stem and twigs was used to treat knife and axe wounds. In addition, the bark has been used to treat colds, for purifying blood, for weight gain and as an analgesic. Finally, sycamore was also taken as cathartic, emetic and anti-diarrheal drug to treat dysentery.

*Platanus occidentalis* L. is a massive perennial tree up to 50 m in height, up to 4 m in diameter and usually found near lakes and streams. Several chemical investigations have shown the presence of triterpene secondary metabolites. This species is also reported to produce betulinic aldehyde, betulinic acid, platanic acid, β-sitosterol, and tiliroside as well as kaempferol 3-O-rhamnosides. Moreover, some polar and non-polar glycosides have been reported from members of the Platanaceae family.

Because of the increasing presence of MRSA-related infections and the lack of acceptable antibiotic therapy, new antibacterial compounds are needed.

SUMMARY OF THE INVENTION

The present invention provides compounds extracted from *Platanus occidentalis*. These compounds were found to exhibit anti-bacterial activity against methicillin resistant *Staphylococcus aureus* (MRSA) and other gram positive bacteria. The compounds of the invention have the general formula I shown below:

(I)

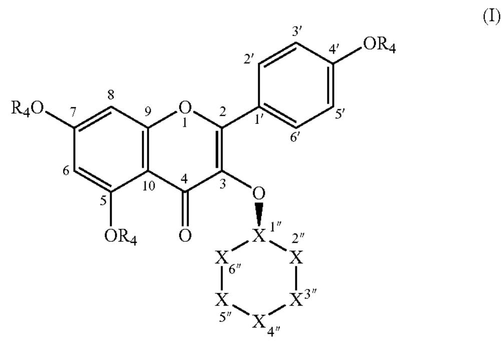

wherein $X_{1'''}$, $X_{2'''}$, $X_{3'''}$, $X_{4'''}$, $X_{5'''}$, $X_{6'''}$ are independently C, $COR_1$, $COR_2$, $COR_3$, CY, N, S, or O;

wherein Y is $CH_3$;

wherein at least one of $X_{1'''}$, $X_{2'''}$, $X_{3'''}$, $X_{4'''}$, $X_{5'''}$, $X_{6'''}$ is N, S or O;

wherein $R_1$, $R_2$ and $R_3$ are independently, hydrogen, halogen, hydroxyl, $C_6$ alkyl, $C_1$-$C_6$ alkoxy, $C_1$-$C_6$ acyloxy, mono, di or tri-$C_1$-$C_6$ alkyl, mono, di or tri-$C_1$-$C_6$ N-alkyl, $C_1$-$C_6$ alkylthiol, $C_1$-$C_6$ acylamino, thiol, nitro, amino, $C_1$-$C_6$ alkylsulfonyl, aminosulfonyl, hydroxy sulfonyl (—$SO_3H$). E-p-coumaroyl, Z-p-coumaroyl;

wherein E-p-coumaroyl has the formula:

(II)

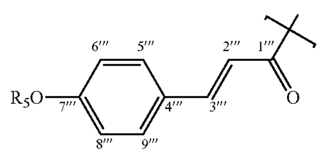

and wherein Z-p-coumaroyl has the formula:

(III)

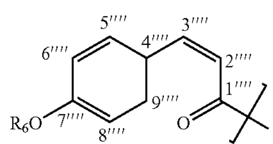

wherein $R_4$, $R_5$ and $R_6$ are independently hydrogen, halogen, hydroxyl, $C_6$ alkyl, $C_1$-$C_6$ alkoxy, $C_1$-$C_6$ acyloxy, mono-$C_1$-$C_6$ alkyl, di-$C_1$-$C_6$ N-alkyl, $C_1$-$C_6$ alkylthiol, $C_1$-$C_6$ acylamino, thiol, nitro, amino, $C_1$-$C_6$ alkylsulfonyl, aminosulfonyl, hydroxy sulfonyl (—$SO_3H$).

The present invention further provides compounds having formula I wherein: $R_1$, $R_2$ and $R_3$ are independently E-p-coumaroyl, Z-p-coumaroyl, hydrogen, $CH_3$, $C_2H_5$, $C_3H_7$, $C_4H_9$, $C_5H_{11}$, $C_6H_{13}$, $C_6H_{10}$, $C_2H_3O_2$, $C_3H_5O_2$, trifluoromethanesulfonate ($CF_3$—$SO_3$—) or benzoyl ($C_6H_5$—C(=O—); and wherein $R_4$, $R_5$ and $R_6$ are independently hydrogen, hydrogen, $CH_3$, $C_2H_5$, $C_3H_7$, $C_4H_9$, $C_5H_{11}$, $C_6H_{13}$, $C_6H_{10}$, $C_2H_3O_2$, $C_3H_5O_2$, trifluoromethanesulfonate ($CF_3$—$SO_3$—) or benzoyl ($C_6H_5$—C(=O—)).

In certain embodiments, the compounds of the present invention have the formula I wherein $R_3$ and $R_4$ are hydrogen and wherein $R_1$ represents E-p-coumaroyl and $R_2$ represents Z-p-coumaroyl; or $R_1$ represents Z-p-coumaroyl and $R_2$ represents E-p-coumaroyl; or $R_1$ and $R_2$ represent Z-p-coumaroyl or $R_1$ and $R_2$ represent E-p-coumaroyl. One compound of the present invention has formula I wherein $R_3$ and $R_4$ are hydrogen and $R_1$ E-p-coumaroyl and $R_2$ represents Z-p-coumaroyl. Another compound of the invention has formula I wherein $R_3$ and $R_4$ are hydrogen and wherein $R_1$ represents Z-p-coumaroyl and $R_2$ represents E-p-coumaroyl. Another compound of the invention has formula I wherein $R_3$ and $R_4$ are hydrogen and wherein $R_1$ and $R_2$ represent Z-p-coumaroyl. In certain embodiments of the present invention the compounds of the present invention are used together as a mixture. An exemplary mixture comprises, consists of or consists essentially of: kaempferol 3-O-α-L-(2",3"-di-E-p-coumaroyl)rhamnoside; kaempferol 3-O-α-L-(2"-E-p-coumaroyl-3"-Z-p-coumaroyl)rhamnoside; kaempferol 3-O-α-L-(2"-Z-p-coumaroyl-3"-E-p-coumaroyl)rhamnoside; and kaempferol 3-O-α-L-(2",3"-di-Z-p-coumaroyl)rhamnoside.

The present invention also provides a method of treating a bacterial infection comprising administering an effective amount of a compound of the present invention or a composition comprising a compound of the invention or a mixture of compounds of the present invention. The bacteria infection may be caused by, for example, but not limited to: *Staphylococcus aureus, Staphylococcus epidermidis, Enterococcus faecium, Enterococcus faecalis, Streptococcus agalactiae, Streptococcus pneumoniae* or *Streptococcus pyogenes*. Any one of these strains may have demonstrated resistance or susceptibility to previously known antibiotics. For example, the strains may be vancomycin-resistant, vancomycin-susceptible, methicillin-resistant, methicillin susceptible, penicillin-resistant, or penicillin-susceptible, or any other antibiotic resistance or susceptibility. In certain embodiments compounds or mixtures of compounds of the present invention are used to treat a bacterial invention caused by *Staphylococcus aureus*, which may be methicillin-resistant, vancomycin-resistant or any other drug resistant strain.

In certain embodiments, a composition comprising a compound of formula I wherein $R_3$ and $R_4$ are hydrogen and wherein $R_1$=$R_2$=E-p-coumaroyl is administered to treat a bacterial infection. In certain embodiments, a composition comprising a compound of the formula I wherein $R_3$ and $R_4$ are hydrogen and wherein $R_1$ represents E-p-coumaroyl and $R_2$ represents Z-p-coumaroyl; or $R_1$ represents Z-p-coumaroyl and $R_2$ represents E-p-coumaroyl; or $R_1$ and $R_2$ represent Z-p-coumaroyl is administered to treat a bacterial infection. In certain embodiments of the present invention compounds of the present invention are used together as a mixture. For example, a composition comprising, consisting of or consisting essentially of the following compounds is administered to treat a bacterial infection: kaempferol 3-O-α-L-(2",3"-di-E-p-coumaroyl)rhamnoside; kaempferol 3-O-α-L-(2"-E-p-coumaroyl-3"-Z-p-coumaroyl)rhamnoside; kaempferol 3-O-α-L-(2"-Z-p-coumaroyl-3"-E-p-coumaroyl)rhamnoside; and kaempferol 3-O-α-L-(2",3"-di-Z-p-coumaroyl)rhamnoside.

The present invention further provides a pharmaceutical composition comprising at least one compound or mixture of compounds of the invention in a pharmaceutically acceptable carrier thereof.

The present invention further provides a method of extracting compounds of the invention from a sycamore tree and/or its parts (for example, from leaves, bark, twigs and small branches).

The present invention also provides a topical or surface disinfectant or antiseptic comprising at least one compound of the present invention alone or in combination with an additional herbal or disinfectant or antiseptic substance. The antiseptic may be used on an animal (i.e. mammal, bird, reptile, etc.) or a surface.

BRIEF DESCRIPTION OF FIGURES

FIG. 1 is a table showing in vitro antimicrobial activity for isolated glycosides and compounds of the present invention compared with known antibiotics.

FIG. 3 is a chart that provides results from in vitro cytotoxicity testing.

FIG. 4 provides exemplary compounds of the present invention.

DETAILED DESCRIPTION

Compounds

Figure 2A:
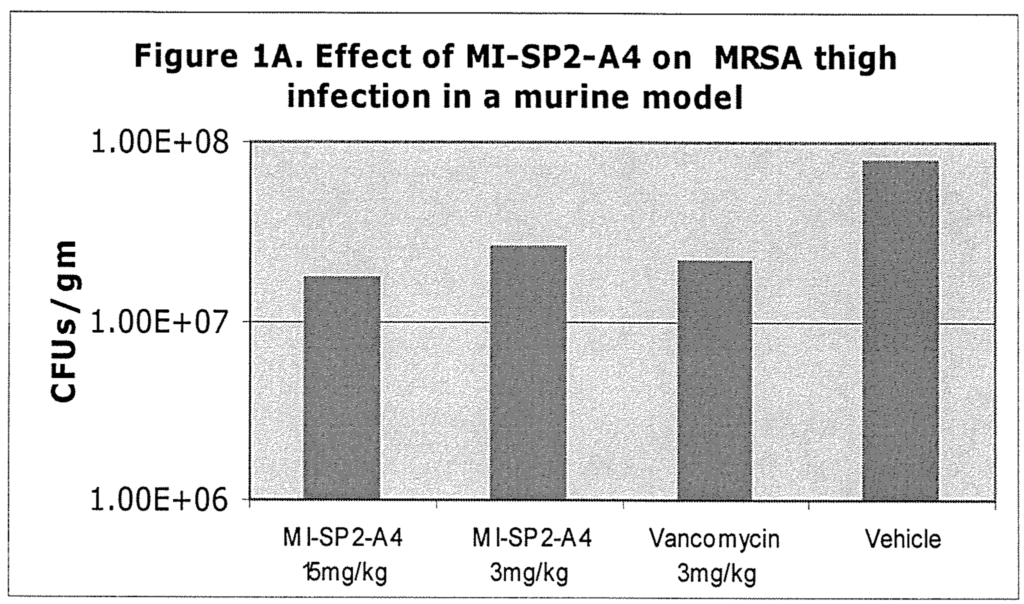
FIG. 2A is a chart that shows the effect of compound 1 on MRSA thigh infection in a murine model.

The present invention provides compounds having the general formula I shown below:

(I)

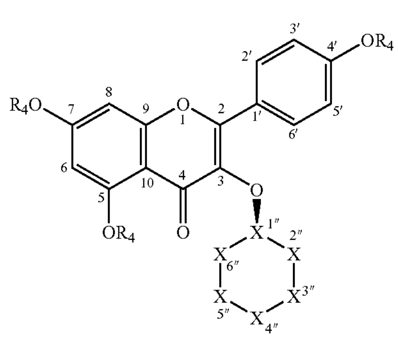

wherein $X_{1''}$, $X_{2''}$, $X_{3''}$, $X_{4''}$, $X_{5''}$, $X_{6''}$ are independently C, $COR_1COR_2$, $COR_3$, CY, N, S, or O;

wherein Y is $CH_3$;

wherein at least one of $X_{1''}$, $X_{2''}$, $X_{3''}$, $X_{4''}$, $X_{5''}$, $X_{6''}$ is N, S or O;

wherein $R_1$, $R_2$ and $R_3$ are independently, hydrogen, halogen, hydroxyl, $C_6$ alkyl, $C_1$-$C_6$ alkoxy, $C_1$-$C_6$ acyloxy, mono, di or tri-$C_1$-$C_6$ alkyl, mono, di or tri-$C_1$-$C_6$N-alkyl, $C_1$-$C_6$ alkylthiol, $C_1$-$C_6$ acylamino, thiol, nitro, amino, $C_1$-$C_6$ alkylsulfonyl, aminosulfonyl, hydroxy sulfonyl (—$SO_3$H), E-p-coumaroyl, Z-p-coumaroyl; wherein E-p-coumaroyl has the formula:

(II)

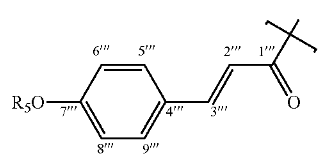

and wherein Z-p-coumaroyl has the formula:

(III)

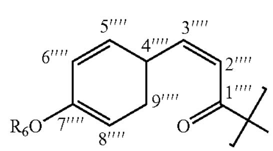

wherein $R_4$, $R_5$ and $R_6$ are independently hydrogen, halogen, hydroxyl, $C_6$ alkyl, $C_1$-$C_6$ alkoxy, $C_1$-$C_6$ acyloxy, mono-$C_1$-$C_6$ alkyl, di-$C_1$-$C_6$ N-alkyl, $C_1$-$C_6$ alkylthiol, $C_1$-$C_6$ acylamino, thiol, nitro, amino, $C_1$-$C_6$ alkylsulfonyl, aminosulfonyl, hydroxy sulfonyl (—$SO_3$H).

In certain embodiments, $R_1$, $R_2$ and $R_3$ are independently E-p-coumaroyl, Z-p-coumaroyl, hydrogen, $CH_3$, $C_2H_5$, $C_3H_7$, $C_4H_9$, $C_5H_{11}$, $C_6H_{13}$, $C_6H_{10}$, $C_2H_3O_2$, $C_3H_5O_2$, trifluoromethanesulfonate ($CF_3$—$SO_3$—) or benzoyl ($C_6H_5$—C(═O—); and wherein $R_4$, $R_5$ and $R_6$ are independently hydrogen, hydrogen, $CH_3$, $C_2H_5$, $C_3H_7$, $C_4H_9$, $C_5H_{11}$, $C_6H_{13}$, $C_6H_{10}$, $C_2H_3O_2$, $C_3H_5O_7$, trifluoromethanesulfonate ($CF_3$—$SO_3$—) or benzoyl ($C_6H_5$—C(═O—).

In other embodiments, compounds of the present invention have the formula I wherein $R_3$ and $R_4$ are hydrogen and wherein $R_1$ represents E-p-coumaroyl and $R_2$ represents Z-p-coumaroyl; or $R_1$ represents Z-p-coumaroyl and $R_2$ represents E-p-coumaroyl; or $R_1$ and $R_2$ represent Z-p-coumaroyl. Where $R_1$ and $R_2$ are E-p-coumaroyl, the present inventors refer to this compound herein as "compound 1."

In a preferred embodiment the compound is kaempferol-3-(2-E,3-Z-di-p-coumaroyl)-rhamnoside (referred to herein as compound 2), kaempferol-3-(2-2-3-E-di-p-coumaroyl)-rhamnoside (referred to herein as compound 3), or kaempferol-3-(2,3-di-Z-p-coumaroyl)rhamnoside (referred to herein as compound 4). In certain embodiments, the present invention provides a mixture comprising compounds of the present invention: kaempferol di-E-p-coumaroyl) rhamnoside; kaempferol 3-O-α-L-(2"-E-p-coumaroyl-3"-Z-p-coumaroyl)rhamnoside; kaempferol 3-O-α-L-(2"-Z-p-coumaroyl-3"-E-p-coumaroyl)rhamnoside; and kaempferol 3-O-α-L-(2",3"-di-Z-p-coumaroyl)rhamnoside.

It is understood that the $OR_1$, $OR_2$ and/or $OR_3$ groups off of any of $X_{1''}$, $X_{2''}$, $X_{3''}$, $X_{4''}$, $X_{5''}$, $X_{6''}$ can be orientated in either the R or S orientation. Any pyranose (6-membered ring having 5 carbons and one oxygen) can be used in the synthesis of these compounds.

Figure 2B:
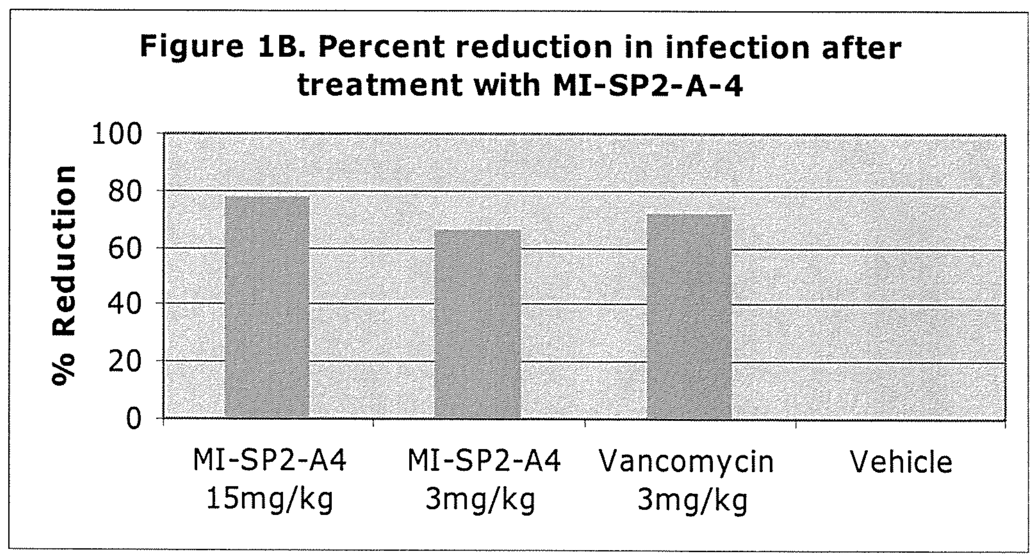
FIG. 2B is a chart that shows the percent reduction in infection after treatment with compound 1.

Ethanolic extracts of various parts of *Platanus occidentalis* were subjected to antimicrobial evaluation, amongst which leaves were found to be non-toxic, highly active and selective against MRSA. Four active compounds (1, 2, 3 and 4) were isolated with the molecular weight 725.2282 $[M+H]^+$, molecular formula ($C_{39}H_{32}O_{14}$), and were shown by $^1$H-NMR and $^{13}$C-NMR to be rhamnose glycosides with different configurations around the rhamnose or olefinic moiety. Results of in vitro evaluation of four compounds of the present invention are provided in FIG. 1. In vivo evaluation of one compound of the present invention is represented in FIGS. 2A and 2B.

Antimicrobial evaluation of the extracts of various parts of *Platanus occidentalis* showed that sycamore leaves contained antibacterial compounds, and were thus purified using bioassay-guided isolation against MRSA. Further fractionation and purification of the ethyl acetate:MeOH (75:25) fraction using HPLC resulted in the isolation of four active metabolites; the structure elucidation for all isolated compounds was performed using LCMS and NMR spectroscopy. Final structure confirmation was accomplished by comparing $^1$H and $^{13}$C NMR data with that reported in the literature.

$^1$H NMR spectra of compounds 1, 2, 3 and 4 clearly displayed the characteristics signals of the kaempferol nucleus and the a-configuration of the rhamnoside sugar. High resolution TOF-ESI-MS of compounds 1, 2, 3 and 4 provided a molecular mass of $[M+H]^+$ at m/z 725.2282 corresponding to the molecular formula ($C_{39}H_{32}O_{14}$). A search using SciFinder Scholar for comparison of $^1$H NMR and $^{13}$C-NMR data with the reference proved that the major glycoside is known as kaempferol 3-O-α-L-(2",3"-di-E-p-coumaroyl) rhamnoside (1) or commonly called platanoside in addition to three new anti-MRSA compounds: kaempferol 3-O-α-L-(2"-E-p-coumaroyl-3"-Z-p-coumaroyl)rhamnoside (2), kaempferol 3-O-α-L-(2"-Z-p-coumaroyl-3"-E-p-coumaroyl) rhamnoside (3), and kaempferol 3-O-α-L-(2",3"-di-Z-p-coumaroyl)rhamnoside (4).

The UV, $^1$HNMR, $^{13}$CNMR of compounds 2, 3 and 4 are highly similar to compound (I). Investigation of HMBC and COSY correlations indicated the positions of attachments of both p-coumaroyl units to L-rhamnose while $^{1}$H NMR coupling constants and NOESY spectra revealed the configurations at C-2''', C-3''' and C-2'''', C-3'''' for the isolated metabolites 2-4. HMBC correlations between H-2" (5.81 Hz), C-1''' (166.6 Hz) as well as H-3" (5.27 Hz), C-1''' (167.3 Hz) and the presence of the COSY correlation between H-2" (5.81 Hz), H-3" (5.27 Hz) confirmed the attachment of both p-coumaroyl units to position 2 and 3. The large coupling constant between H-2''' and H-3''' (15.6 Hz) in the known compound, 1 indicated the trans relationship at both p-coumaroyl units attached to both positions 2 and 3 at L-rhamnose. For glycoside 2, HMBC correlations between H-2" (5.78 Hz), C-1''' (166.4 Hz) as well as H-3" (5.27 Hz), C-1'''' (166.1 Hz) and the presence of the COSY correlation between H-2" (5.78 Hz), H-3" (5.27 Hz) confirmed the attachment of both p-coumaroyl units to position 2 and 3. The J value between H-2''' and H-3''' (16.0 Hz) of the p-coumaroyl functionality at position 2 of the L-rhamnose indicated an E configuration while the J value between H-2'''' and H-3'''' (12.8 Hz) on the p-coumaroyl attached to position 3 of the L-rhamnose indicated a Z configuration, which was also confirmed by the NOE correlation between H-2'''' and H-3''''. The opposite arrangement was shown for glycoside 3, where HMBC correlations between H-2" (5.78 Hz), C-1'''' (165.2 Hz) as well as H-3" (5.27 Hz), C-1''' (167.3 Hz) and the presence of the COSY correlation between H-2" (5.78 Hz), H-3" (5.27 Hz) confirmed the attachment of both p-coumaroyl units to position 2 and 3. The J value between H-2''' and H-3''' (16.0 Hz) of the p-coumaroyl functionality at position 3 of L-rhamnose supported the E relationship, while the J value between H-2'''' and H-3'''' (12.8 Hz) of the p-coumaroyl functionality at position 2 of L-rhamnose suggested a Z-relationship, which was also confirmed by the NOE correlation between H-2'''' and H-3''''. HMBC correlations in glycoside 4 between H-2" (5.79 Hz), C-1'''' (166.1 Hz) as well as H-3" (5.21 Hz), C-1'''' (166.2 Hz) and the presence of the COSY correlation between H-2" (5.79 Hz), H-3" (5.21 Hz) confirmed the attachment of both p-coumaroyl units to positions 2 and 3. The small coupling constants (12.8 Hz) for glycoside 4 between H-2'''' and H-3'''' established the Z configuration[18] of both p-coumaroyl groups at positions 2 and 3 of L-rhamnose; this was also confirmed by the NOE correlations between H-2'''' and H-3''''. The absolute configuration of the sugar was showed to be L-rhamnose by GC comparison of its acetylated thiazolidine derivative with that of an L-rhamnose standard. See Ibrahim et al, Methicillin-resistant *Staphylococcus aureus* (MRSA)-active Metabolites from *Platanus occidentalis* (American Sycamore), herein incorporated by reference in its entirety.

The in vitro antimicrobial activity for the isolated glycosides is represented in FIG. 1. A modified version of CLSI (formerly NCCLS) method was used for the in vitro evaluation of test samples. Duplicate samples were transferred to 96-well microplates after diluting with 0.9% saline. The microbial cell suspensions were to give the desired target inocula after addition to the samples. Media and solvent controls were included in each assay. The $IC_{50}$ was calculated by plotting percent growth versus test concentration. Of the four compounds, compound (4) showed the most potent in vitro activity, indicating that the configuration of the double bond of the coumaroyl moiety is important for bioactivity. All compounds were inactive against other test organisms including the Gram negative bacteria *E. coli* and *Pseudomonas aeruginosa*, as well as against *Mycobacterium intracelluare*, in addition to the fungi *Candida albicans, Candida glabrata, Candida krusei, Cryptococcus neoformans* and *Aspergillus fumigatus* at the highest test concentration of 20 μg/mL. These compounds demonstrate a unique specificity for MRSA.

Compositions

The present invention also provides compositions comprising a compound or comprising mixtures of the compounds of the present invention. The term "comprising" as used herein in the detailed description is meant to convey that other embodiments of the invention may also either "consist essentially of" or "consist of."

In certain embodiments, the compositions (used in either/or a method of treating a bacterial infection, used as a disinfectant or antiseptic or used in as a pesticide, which are all discussed herein below) of the present invention comprise, consist of or consist essentially of compounds having the formula I wherein $R_3$ and $R_4$ are hydrogen and wherein $R_1$ represents E-p-coumaroyl and $R_2$ represents Z-p-coumaroyl; or $R_1$ represents Z-p-coumaroyl and $R_2$ represents E-p-coumaroyl; or $R_1$ and $R_2$ represent Z-p-coumaroyl or $R_1$ and $R_2$ represent E-p-coumaroyl. One composition of the present invention comprises, consists of or consists essentially of compounds of the present invention having formula I wherein $R_3$ and $R_4$ are hydrogen and $R_1$ E-p-coumaroyl and $R_2$ represents Z-p-coumaroyl. Another composition of the present invention comprises, consists of or consists essentially of a compound of the invention has formula I wherein $R_3$ and $R_4$ are hydrogen and wherein $R_1$ represents Z-p-coumaroyl and $R_1$ represents E-p-coumaroyl. Another composition of the present invention comprises, consists of or consists essentially of a compound having formula I wherein $R_3$ and $R_4$ are hydrogen and wherein $R_1$ and $R_2$ represent Z-p-coumaroyl. In certain embodiments of the present invention the composition comprises compounds of the present invention are used together as a mixture. An exemplary mixture comprises, consists of or consists essentially of: kaempferol 3-O-α-L-(2",3"-di-E-p-coumaroyl)rhamnoside; kaempferol 3-O-α-L-(2"-E-p-coumaroyl-3"-Z-p-coumaroyl)rhamnoside; kaempferol 3-O-α-L-(2"-Z-p-coumaroyl-3"-E-p-coumaroyl)rhamnoside; and kaempferol 3-O-α-L-(2",3"-di-Z-p-coumaroyl) rhamnoside.

In certain embodiments, the composition comprises at least two compounds of the present invention. In other embodiments the composition may comprise at least 2 to 6 compounds of the present invention. In other embodiments, the composition comprises more than 2 compounds of the present invention. It may be beneficial to have more than one compound of the invention in the composition to prevent the development of resistant strains. In certain embodiments, a mixture of compounds comprises the following compounds: kaempferol 3-O-α-L-(2",3"-di-E-p-coumaroyl)rhamnoside; kaempferol 3-O-α-L-(2"-E-p-coumaroyl-3"-Z-p-coumaroyl) rhamnoside; kaempferol 3-O-α-L-(2"-Z-p-coumaroyl-3"-E-p-coumaroyl)rhamnoside; and kaempferol 3-O-α-L-(2",3"-di-Z-p-coumaroyl)rhamnoside.

Compositions of the invention may be used in, but not limited to, pharmaceutical, agricultural or sanitation settings. The compositions can be used in methods to treat bacterial infections, or can be used as topical or surface disinfectants or antiseptics, or can be used in a pesticide in an agricultural setting. Depending on the use, the compositions may further contain acceptable carriers. For example, a pharmaceutical composition of the present invention comprises at least one compound of the present invention and may further comprise a pharmaceutically acceptable carrier. Such carriers, buffers, excipients, and antioxidants, flavorings. etc. are known in the art. Compounds of the present invention can be formulated according to known methods for preparing pharmaceutically useful compositions. Formulations are described in detail in a number of sources that are well known and readily available to those skilled in the art. For example, Remington's Pharmaceutical Science by E. W. Martin describes formulations that can be used in connection with the present invention. In general, compositions of the present invention will be formulated such that an effective amount of compound(s) of the present invention are combined with a suitable carrier to facilitate effective administration of the composition.

In accordance with the invention, pharmaceutical compositions comprising, as the active ingredient, an effective amount of one or more of the subject compounds and one or more non-toxic, pharmaceutically acceptable carriers or diluents, can be used by persons of ordinary skill in the art. In addition, the pharmaceutical composition can comprise one or more of the compounds of the present invention as a first active ingredient together with a second or third active ingredient comprising an anti-infective or anti-bacterial compound known in the art.

The most effective mode of administration and dosage regimen will depend upon the severity of the infection and course of that condition, previous therapy, the patient's health status and response, as well as the judgment of the treating physician. Compositions of the invention may be administered to the patient at one time or over a series of treatments.

The present pharmaceutical compositions may comprise a compound of the invention or a derivative or analog or an optical isomer or racemate or tautomer thereof or a pharmaceutically acceptable salt thereof, optionally in admixture with a pharmaceutically acceptable diluent or carrier.

Any of the compounds of the invention, derivatives or analogs, or compositions can be administered to a subject, such as an animal host, including a human patient, by it self, or in pharmaceutical compositions where it is mixed with suitable carriers or excipient(s) at doses therapeutically effective to treat or ameliorate a bacterial infection. A therapeutically effective dose further refers to that amount of the compound sufficient to result in amelioration of symptoms associated with the infection. Techniques for formulation and administration of the compounds of the instant application may be found in "Remington's Pharmaceutical Sciences," Mack Publishing Co. Easton, Pa., latest edition.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ (the dose where 50% of the cells show the desired effects) as determined in cell culture. Such information can be used to more accurately determine useful doses in humans.

A therapeutically effective dose refers to that amount of the compound that result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). Dosage amount and interval may be adjusted individually to provide plasma levels of the active moiety which are sufficient to maintain the desired effects.

In cases of local administration or selective uptake, the effective local concentration of the drug may not be related to plasma concentration. The amount of composition administered will, of course, be dependent on the subject being treated, on the subject's weight, the severity of the affliction, the manner of administration and the judgment of the prescribing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations, which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion.

Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example) as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions.

Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

Disinfectant/Antiseptic Compositions

Compounds of the present invention can also be used in compositions for use as a topical or surface disinfectant or antiseptic. The antiseptic can be used on a mammal, including a human. The compositions of the present invention may further include herbal or additional disinfectant or antiseptic substances.

Compositions of the present invention may be used in sanitizing a surface, for example in a hospital room or ward. In such cases the composition is applied to the surfaces. The composition may be either a solution or an emulsion in suitable liquid carriers or it may be formulated for spray application. The spray application may also be an electrostatic spray, using an appropriate solvent or solvent system known to those skilled in the art. A spray may also be used, for example, for dispensing a composition of the present invention onto a hand (or other part) of a person. An electrostatic spray application to a hand may be used, with advantage, where a substantially uniform coverage of antiseptic is particularly important e.g. to a surgeon during "scrubbing up" before surgery. The liquids for applying to a surface, by spraying or otherwise, in accordance with the invention may contain, apart from the solvent(s) and/or other liquid carrier(s), other components as necessary or desirable for the intended purpose. Thus, a second or further antiseptic or disinfectant (including from an herbal or other natural origin) may be included, as well as additional substances such as, but not limited to surfactants and fragrances etc. In general, the non-active ingredients of the compositions of the invention may be identical to known compositions for the purpose except that they contain compounds of the present invention in whole or part substitution for one or more of, the other active ingredients. Compounds or compositions of the present invention may also be included as a component in household detergents, cleansers and creams, for example, washing powders or conditioners and hand gels. Again, the compounds may be included in what are otherwise standard or known compositions for the purpose concerned. The compounds of the present invention may be an extra ingredient or in partial or complete replacement of a standard ingredient. The compositions may already contain a disinfectant or antiseptic and the compounds of the present invention may be added to give an extra or extended antiseptic effect.

In addition, compounds of the present invention may be impregnated into household objects that may be prone to microbial infestation, e.g. dishcloths, plastic soap dishes, surfaces used for the preparation of food. For these purposes, the compounds may be included during manufacture of the object, e.g. in mixtures for plastics moldings or the like, or it may be applied to the object after manufacture, e.g. by soaking dishcloths in compositions of the invention. The presence of the compound(s) at the surface of the object will provide the desired antiseptic effect.

Agricultural

The present invention further provides compositions comprising at least one compound of the present invention for agricultural applications, for example as use in a pesticide (herbicides, insecticides, fungicides, bactericides, molluscicides, and nematicides). For example, compounds and compositions of the present invention are also useful in agricultural applications to protect plants and crops against insects, viruses, fungi, weeds and other undesirable pests. The compounds and compositions may be applied to a plant, either topically such as by spraying or through watering for systemic applications.

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient (composition of the present invention), mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro) encapsulated and further formed into a suspension or solid formulation; alternatively the entire formulation of active ingredient can be encapsulated (or "overcoated"). Encapsulation can control or delay release of the active ingredient.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Accordingly, the present invention provides a method of controlling pests and/or weeds in a crop by administering compounds or compositions of the present invention to the crop.

Method of Treating Bacterial Infection

The present invention also provides a method of treating a bacterial infection in a subject comprising administering an effective amount of any one of the compounds or a mixture comprising at least one compound of the present invention. The subject can be any mammal including a human. The bacteria infection may be caused by, for example, but not limited to: *Staphylococcus aureus, Staphylococcus epidermidis, Enterococcus faecium, Enterococcus faecalis, Streptococcus agalactiae, Streptococcus pneumoniae* or *Streptococcus pyogenes*. Any one of these strains may have demonstrated resistance or susceptibility to previously known antibiotics. For example, the strains may be vancomycin-resistant, vancomycin-susceptible, methicillin-resistant, methicillin susceptible, penicillin-resistant, or penicillin-susceptible, or any other antibiotic resistance or susceptibility. In certain embodiments compounds or mixtures of compounds of the present invention are used to treat a bacterial invention caused by *Staphylococcus aureus*, which may be methicillin-resistant, vancomycin-resistant *Staphylococcus aureus* infection.

The present invention also provides methods of treating a bacterial infection in a subject comprising administering an effective amount of at least one compound or mixtures of compounds of the invention. As used herein, treating means either an improvement in condition, reduction of symptoms and even complete eradication of the infection. In certain embodiments, it may be preferably to administer a combination of more than 2 and even up to more than 6 (but not limited to 6) compounds of the present invention. This may help reduce the chances of the bacteria developing resistance to the compounds. The subject may be treated with compounds or compositions of the invention at the same time or may be treats sequentially with different compounds or compositions of the invention.

In certain embodiments, the method of treatment comprises administering a compound of formula I wherein $R_1=R_2=$E-p-coumaroyl.

In certain embodiments the bacteria infection is caused by *Staphylococcus aureus*. The *Staphylococcus aureus* may methicillin-resistant, vancomycin-resistant, or may be any other drug resistant strain.

Methods of Extracting

The present invention also provides a method of extracting the compounds of the invention from a sycamore tree and/or its parts, such as leaves, bark, twigs and small branches. The method comprises mixing sycamore tree parts, such as leaves with a first aqueous rich liphophilic solvent for a length of time sufficient to remove undesired highly hydrophilic compounds. Depending on the mixing conditions and the ratio of leaves to solvent and temperature of the solution, generally about two hours is sufficient. The first aqueous rich liphophilic solvent is removed and a second aqueous rich liphophilic solvent is added and mixed for a time sufficient to extract the compounds. Depending on the mixing conditions and the ratio of leaves to solvent and temperature of the solution, generally about two hours is sufficient. Finally the volume of the aqueous rich liphophilic solvent is reduced to cause precipitation of the compounds of the present invention.

The first aqueous rich liphophilic solvent may be, but is not limited to, EtOH:$H_2O$, carbon dioxide:$H_2O$, lower alcohol:$H_2O$s and a mixture of other aliphatics (carbon-hydrogen linear compounds) in $H_2O$. Aliphatics are known in the art and include, but are not limited to, alkanes, alkenes, and alkynes. In certain embodiments, the first aqueous rich liphophilic solvent comprises EtOH:$H_2O$ (25:75). In certain embodiments, the second aqueous rich liphophilic solvent comprises EtOH:$H_2O$ (75:25).

EXAMPLES

Example 1

Extraction and Isolation

Ten kg of dried leaves, bark, and branches of *P. occidentalis* of different sizes were extracted at room temperature with ethanol yielding a 400 g extract residue. An aliquot of 50 g of ethanolic extract was loaded onto a 1 kg silica gel column and subjected to vacuum liquid chromatography. Gradient elution was carried out initially with hexane and increasing polarity with hexane:EtOAc, EtOAc, ETOAc:MeOH, MeOH and MeOH:$H_2O$. A total of nine fractions were obtained including the active fraction EtOAc:MeOH (7 g), from which (4 μm) was further purified on HPLC, C8 column (250×150 mm) by $H_3CN$: $H_2O$:MeOH yielding active fraction (275 mg). The active fraction was further purified using an amino column (250×21.20 mm) using hexane/DCM/MeOH system which purified as 3 well resolved peaks, one of them representing two compounds. Final purification and isolation of the major glycoside compound (1) was carried out by applying isocratic mode on amino column (250×21.20 mm) using DCM:MeOH (25:75) while the final purifications of glycoside (2), (3) and (4) were done using PFP (Pentafluoro phenyl) (250×10 mm) column using $CH_3CN$:$H_2O$:MeOH.

The carbohydrate analysis: 0.3 mg of each glycoside alone was hydrolyzed with 2N HCl (1 ml) for 3 hours at 95° C. cooling, neutralize with $NH_4OH$ and then extracted using EtOAc/$H_2O$. The aqueous layer was dried then dissolved in pyridine (0.3 ml) and 0.1 M in pyridine L-cysteine methyl ester hydrochloride. The reaction mixture was heated for 1 hour at 60° C. then an equal volume of $AC_2O$ was added with continuous heating for extra 1 hour. The acylated thiazolidine derivatives were subjected to GC analysis capillary column: DB-5 ms (30 m×0.25 mm×0.25 μm). The sugars were identified as L-rhamnose as compared with the standard.

Example 2

In Vivo MRSA Assay

The in vivo antimicrobial activity for the isolated glycosides is represented in FIGS. 2A and 2B. Mice (CD-1) were purchased from Harlan Inc. and acclimatized up to 5 days before use. Food and water were available ad libitum throughout the study. They were rendered neutropenic by two injections of cyclophosphamide (100 mg/kg) given intraperitoneally, one and four days before infection. A volume of 50 uL suspension of Methicillin-resistant *Staphylococcus aureus* ($1.5\times10^6$ live organisms) was injected intramuscularly (1M) into each of the two rear thighs. Each thigh was considered as an individual data point (total of 4 data points for each treatment). These mice were randomly distributed into the control or treatment groups (n=2/group).

Treatment with the test compound (1) was initiated via the intraperitoneal route 2 hrs after thigh inoculation. Control animals were concurrently administered saline (mock treatment) or vancomycin in the same volume as those receiving compound (1). All animals were sacrificed after 48 hours by $CO_2$ inhalation. Immediately following sacrifice, thigh tissue was collected from the animals, weighed, and homogenized in 5.0 mL of saline. Thigh muscle homogenate was then processed for microbiological assay to determine the number of MRSA cfu per gram of muscle tissue.

FIGS. 2A and 2B provide the in vivo results of compound (I), which demonstrated that in the muscle tissue of untreated control animals (vehicle group) the MRSA cfu/g was $8.02\times10^7$. The number of MRSA isolated from vancomycin treated animals was $2.2\times10^7$ g of tissue, a reduction of 72% compared to vehicle control. Similarly, the number of MRSA recovered after treatment with compound (I) at 3 mg/kg and 15 mg/kg were $2.6\times10^7$ and $1.8\times10^7$ respectively, which correspond to a reduction of 67% and 78% as compared to vehicle control. These results confirm the in vitro data and indicate that the test compound has shown equal efficacy compared to vancomycin at the doses tested. To determine the maximum tolerated dose in the preliminary experiment, a maximum of 20 mg/kg of compound (1) was giving IP for two days. No untoward effect was seen in these animals indicating no acute toxicity.

Example 3

Cytotoxicity Testing

FIG. 3 provides the results of cytotoxicity testing in a panel of cell lines that were incubated with test compounds for 48 hours and cell viability was determined. The cytotoxicity of compound (1) and a mixture of compounds (1), (2), (3) and (4) was tested at high concentrations to determine at what concentration the compounds became cytotoxic. Stock solutions were prepared at 20 mg/ml in DMSO. Cytotoxicity was tested up to a highest concentration of 100 μg/ml. In a routine assay, a stock solution of 2 mg/ml is used and the highest test concentration is 10 μg/ml. The results from the in vitro cytotoxicity testing are set forth in FIG. 3. The results show that the compounds of the present invention are much less cytotoxic (about 100 times less toxic) than doxorubicin, which was used as a positive control for comparing the toxic effect of these compounds.

Example 4

In Vitro Minimal Inhibitory Concentration Against Representative Strains of Gram-Positive Bacteria The in vitro minimal inhibitory concentration (MIC) of certain compounds and mixtures of compounds of the present invention were tested against representative strains of gram-positive bacteria.

Materials And Methods

Test Compounds

The test agents, lot numbers, storage conditions, and test concentration ranges were as follows:

| Test Article | Supplier | Catalog No | Lot No. | Storage Temp. | Concentration Ranges Tested (μg/mL) |
|---|---|---|---|---|---|
| MI-G1-E,E | University of Mississippi | | | −20° C. | 64-0.06 |

-continued

| Test Article | Supplier | Catalog No | Lot No. | Storage Temp. | Concentration Ranges Tested (μg/mL) |
|---|---|---|---|---|---|
| MI-G4-Z,Z | University of Mississippi | | | −20° C. | 64-0.06 |
| MI-Mix | University of Mississippi | | | −20° C. | 64-0.06 |
| Linezolid | ChemPacifica | 35710 | CHPC091007-01 | 4° C. | 64-0.06 |

MI-G1-E,E=kaempferol 3-O-α-L-(2",3"-di-E-p-coumaroyl)rhamnoside; kaempferol 3-O-α-L-(2"-E-p-coumaroyl-3"-Z-p-coumaroyl)rhamnoside; MI-G4-Z,Z=kaempferol 3-O-α-L-(2",3"-di-Z-p-coumaroyl)rhamnoside; and MI-Mix=a mixture containing of the following compounds: kaempferol 3-O-α-L-(2",3"-di-E-p-coumaroyl)rhamnoside; kaempferol E-p-coumaroyl-3"-Z-p-coumaroyl)rhamnoside; kaempferol 3-O-α-L-(2"-Z-p-coumaroyl-3"-E-p-coumaroyl) rhamnoside; and kaempferol 3-O-α-L-(2",3"-di-Z-p-coumaroyl)rhamnoside.

All test articles were dissolved in DMSO. Stock solutions were prepared at 40-fold the highest concentration in the test plate. The final concentration of DMSO in the test system was 2.5%.

Organisms

The test organisms were obtained from clinical laboratories; quality control isolates were from the American Type Culture Collection (Manassas, Va.). Organisms were streaked for isolation on agar medium appropriate to each organism. Colonies were picked by swab from the isolation plates and put into suspension in appropriate broth containing a cryoprotectant. The suspensions were aliquoted into cryogenic vials and maintained at −80° C.

The isolates were streaked from the frozen vials onto appropriate medium: Trypticase Soy Agar (Becton-Dickinson, Sparks, Md.) for most organisms or Trypticase Soy Agar plus 5% sheep blood (Cleveland Scientific, Bath, Ohio) for streptococci. The plates were incubated overnight at 35° C.

Test Media

The medium employed for the MIC assay was Mueller Hinton II Broth (MHB II-Becton Dickinson, #212322, Lot #9044411) for most of the organisms. MHB II was supplemented with 2% lysed horse blood (Cleveland Scientific Lot #22299-1) to accommodate the growth of *Streptococcus pneumoniae, Streptococcus pyogenes* and *Streptococcus agalactiae*. The media were prepared at 102.5% the normal weight to offset the dilution created by the addition of 5 μL drug solution to each well of the microdilution panels.

Test Procedure

The MIC assay method followed the procedure described by the Clinical and Laboratory Standards Institute (see Clinical and Laboratory Standards Institute. Methods for Dilution Antimicrobial, Susceptibility Tests for Bacteria That Grow Aerobically; Approved Standard—Eighth Edition. CLSI document M07-A8 [ISBN 1-56238-689-1]. Clinical and Laboratory, Standards Institute, 940 West Valley Road, Suite 1400, Wayne, Pa. 19087-1898 USA, 2009) and employed automated liquid handlers to conduct serial dilutions and liquid transfers. Automated liquid handlers included the Multidrop 384 (Labsystems, Helsinki, Finland), Biomek 2000 and Multimek 96 (Beckman Coulter, Fullerton Calif.).

The wells of Columns 2-12 of standard 96-well microdilution plates (Falcon 3918) were filled with 150 μL of DMSO on the Multidrop 384. The drugs (300 μL) were dispensed into Column 1 of the appropriate row in these plates. These would become the mother plates from which the test plates (daughter plates) were prepared. The Biomek 2000 completed serial transfers through Column 11 in the mother plates. The wells of Column 12 contained no drug and were the organism growth control wells in the daughter plates. The daughter plates were loaded with 185 μL of the appropriate test media (described above) using the Multidrop 384. The daughter plates were prepared on the Multimek 96 instrument which transferred 5 μL of drug solution from each well of a mother plate to each corresponding well of each daughter plate in a single step. Therefore, the test agents were maintained in solution in 100% DMSO up until the point of being added to the final test medium.

Standardized inoculum of each organism was prepared per CLSI methods (See Clinical and Laboratory Standards Institute. Performance Standards for Antimicrobial Susceptibility Testing; Nineteenth Informational Supplement. CLSI document M100-S19 [ISBN 1-56238-690-5]. Clinical and Laboratory Standards Institute, 940 West Valley Road, Suite 1400, Wayne, Pa. 19087-1898 USA, 2009.). Suspensions were prepared in MHB to equal the turbidity of a 0.5 McFarland standard. The suspensions were diluted 1:9 in broth appropriate to the organism. The inoculum for each organism was dispensed into sterile reservoirs divided by width (Beckman Coulter), and the Biomek 2000 was used to inoculate the plates. Daughter plates were placed on the Biomek 2000 work surface reversed so that inoculation took place from low to high drug concentration. The Biomek 2000 delivered 10 μL of standardized inoculum into each well. This yielded a final cell concentration in the daughter plates of approximately $5\times10^5$ colony-forming-units/mL. Thus, the wells of the daughter plates ultimately contained 185 μL of broth, 5 μL of drug solution, and 10 μL of bacterial inoculum. The final concentration of DMSO in the assay plate was 2.5%.

Plates were stacked 3 high, covered with a lid on the top plate, placed in plastic bags, and incubated at 35° C. for approximately 18 hours for most of the isolates. The *Streptococcus* plates were read after 20 hours of incubation. The microplates were viewed from the bottom using a plate viewer. For each of the test media, an un-inoculated solubility control plate was observed for evidence of drug precipitation. The MIC was read and recorded as the lowest concentration of drug that inhibited visible growth of the organism.

Results And Discussion

The MIC results are summarized in Table 1. The linezolid results for the quality control strains showed that linezolid values fell within the published quality control guidelines. The linezolid values for the other test strains were typical of linezolid activity against these species.

The MIC results for the tested compounds of the present invention showed some insolubility in the final test panels when at a higher concentration. As shown in the footnotes to Table 1, depending upon the test agent and the test medium, there was evidence of precipitation in the solubility control plate at the higher concentrations tested. The MIC values were not read at test concentrations where visible precipitation was evident, which limited the range of test concentrations where an MIC value could be recorded. Therefore, even though the concentration range tested was 64-0.06 μg/mL, in most instances the MIC reading had to be limited to concentrations less than 64 μg/mL. The maximum concentration included depended upon the agent and test medium.

Compound MI-Mix demonstrated activity against only a few of the test strains at the highest concentrations considered. The activity was limited to several strains of enterococci, and MICs were in the range of 4-8 μg/mL.

The other two agents MI-G1-E,E and MI-G4-Z,Z demonstrated a profile of activity that was similar to each other. Against *S. aureus*, the agents were inactive at the highest concentration considered (MIC>8 μg/mL). Activity was demonstrated against some strains of *S. epidermidis* in the range of 4-8 μg/mL. Both agents inhibited multiple strains of enterococci that included *E. faecalis* and *E. faecium*, and vancomycin-susceptible and vancomycin-resistant strains of each species. Compound M1-G1-E,E appeared to be slightly more active than M1-G4-Z,Z against these organisms. Neither compound was active at the highest concentrations considered for MIC readings against the streptococci.

In conclusion, the test agents of the present invention demonstrated in vitro activity against some test strains of Gram-positive bacteria.

TABLE 1

Minimal Inhibitory Concentration (MIC) Values for Investigational Agents and the Comparator Agent Linezolid

| Organism | MMX No. | Phenotype1 | Source2 | MIC (μg/ml) MI-G1-E,E[3,4] | MI-G4-Z,Z[5,6] | MI-Mix7,8 | Linezolid |
|---|---|---|---|---|---|---|---|
| *Staphylococcus aureus* | 100 | CLSI QC | ATCC 29213 | >8 | >8 | >16 | 4[9] |
| | 753 | MSSA | CHP | >8 | >8 | >16 | 4 |
| | 3856 | MSSA | Mt. Sinai | >8 | >8 | >16 | 4 |
| | 2063 | MSSA | UCLA | >8 | >8 | >16 | 2 |
| | 758 | MRSA | CHP | >8 | >8 | >16 | 4 |
| | 3894 | MRSA | Mt. Sinai | >8 | >8 | >16 | 4 |
| | 2055 | MRSA | UCLA | >8 | >8 | >16 | 4 |
| *Staphylococcus epidermidis* | 3703 | MSSE | CHP | 4 | 8 | >16 | 1 |
| | 3763 | MSSE | Mt. Sinai | 4 | 8 | >16 | 2 |
| | 835 | MSSE | UCLA | 4 | 8 | >16 | 1 |
| | 762 | MRSE | CHP | >8 | >8 | >16 | 1 |
| | 3752 | MRSE | Mt. Sinai | >8 | >8 | >16 | 1 |
| | 826 | MRSE | UCLA | 8 | >8 | >16 | 1 |
| *Enterococcus faecium* | 0799 | VSE | CHP | >8 | >8 | >16 | 2 |
| | 1259 | VSE | Mt. Sinai | >8 | >8 | 8 | 4 |
| | 0845 | VSE | UCLA | 1 | 4 | 4 | 2 |
| | 4024 | VRE | CHP | >8 | >8 | >16 | 4 |
| | 1238 | VRE | Mt. Sinai | 0.5 | 4 | 4 | 2 |
| | 4048 | VRE | UCLA | >8 | >8 | >16 | 4 |
| *Enterococcus faecalis* | 101 | CLSI QC | ATCC 29212 | 8 | 8 | >16 | 2[10] |
| | 742 | VSE | CHP | >8 | >8 | >16 | 2 |
| | 3896 | VSE | Mt. Sinai | 4 | >8 | >16 | 1 |
| | 3199 | VSE | UCLA | 4 | >8 | >16 | 2 |
| | 4131 | VRE | CHP | 1 | 4 | 4 | 2 |
| | 3821 | VRE | Mt. Sinai | 4 | 8 | >16 | 2 |
| | 4160 | VRE | UCLA | 4 | 8 | >16 | 2 |
| *Streptococcus agalactiae* | 4106 | — | CHP | >16 | >32 | >32 | 2 |
| | 3743 | — | Mt. Sinai | >16 | >32 | >32 | 1 |
| | 4093 | — | UCLA | >16 | >32 | >32 | 1 |
| *Streptococcus pneumoniae* | 1195 | CLSI QC | ATCC 49619 | >16 | >32 | >32 | 1[11] |
| | 866 | PSSP | CHP | >16 | >32 | >32 | 1 |
| | 3937 | PSSP | Mt. Sinai | >16 | >32 | >32 | 1 |
| | 3130 | PSSP | UCLA | >16 | >32 | >32 | 1 |
| | 748 | PRSP | CHP | >16 | >32 | >32 | 0.5 |
| | 3953 | PRSP | Mt. Sinai | >16 | >32 | >32 | 0.5 |
| | 3160 | PRSP | UCLA | >16 | >32 | >32 | 1 |
| *Streptococcus pyogenes* | 718 | — | CHP | >16 | >32 | >32 | 1 |
| | 3928 | — | Mt. Sinai | >16 | >32 | >32 | 1 |
| | 2572 | — | UCLA | >16 | >32 | >32 | 1 |

Footnotes to Table 1:

[1]Phenotype: CLSI QC; Clinical and Laboratory Standards Institute recommended quality control strain; MSSA, methicillin-susceptible *Staphylococcus aureus*; MRSA, methicillin-susceptible *Staphylococcus aureus*; MSSE, methicillin-susceptible *Staphylococcus epidermidis*; MRSE, methicillin-resistant *Staphylococcus epidermidis*; VSE, vancomycin-susceptible *Enterococcus*; VRE, vancomycin-resistant *Enterococcus*; PSSP, penicillin-susceptible *Streptococcus pneumoniae*; PRSP, penicillin-resistant *Streptococcus pneumoniae*

[2]Source: ATCC, American Type Culture Collection; CHP, Clarian Health Partners, Indianapolis, IN; Mt. Sinai, Mt. Sinai Medical Center, New York, NY; UCLA, University of California at Los Angeles Medical Center, Los Angelkes, CA

[3]Precipitation was observed at 64, 32 and 16 μg/mL in MHB

[4]Precipitation was observed at 64 and 32 μg/mL in MHB with 2% Laked Horse Blood

[5]Precipitation was observed at 64, 32 and 16 μg/mL in MHB

[6]Precipitation was observed at 64 μg/mL in MHB with 2% Laked Horse Blood

[7]Precipitation was observed at 64 and 32 μg/mL in MHB

[8]Precipitation was observed at 64 μg/mL in MHB with 2% Laked Horse Blood

[9]CLSI Acceptable limits for linezolid versus S aureus ATCC 29213 = 1-4 μg/mL

[10]CLSI Acceptable limits for linezolid versus E. faecalis ATCC 29212 = 1-4 μg/mL

[11]CLSI Acceptable limits for linezolid versus S. pneumoniae ATCC 49619 = 0.5-2 μg/mL

We claim:

1. A composition comprising a mixture of kaempferol3-0-α-L-(2",3"-di-E-p-coumaroyl)-rhamnoside; kaempferol 3-0-α-L-(2"-E-p-coumaroyl-3"-Z-p-coumaroyl)-rhamnoside; kaempferol 3-0-α-L-(2"-Z-p-coumaroyl-3"-E-p-coumaroyl)-rhamnoside; and kaempferol 3-0-α-L-(2",3"-di-Z-p-coumaroyl)-rhamnoside.

2. A topical or surface disinfectant comprising at least one compound or mixtures of compounds of claim 1 alone or in combination with an additional herbal or disinfectant.

3. The antiseptic of claim 2 for use on a mammal.

4. A compound comprised of a formula

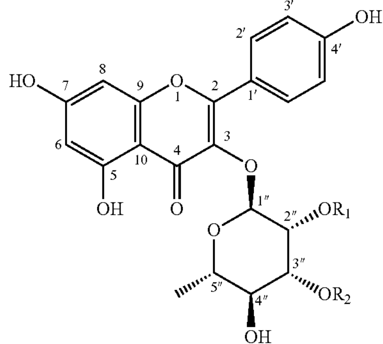

Z-p-coumaroyl $R_1$=$R_2$=Z-p-coumaroyl.

5. A topical or surface disinfectant comprising the compound of claim 4 alone or in combination with an additional herbal or disinfectant.

6. The disinfectant of claim 5 for use on a mammal.

* * * * *